United States Patent [19]

Saukaitis

[11] 4,199,346
[45] Apr. 22, 1980

[54] HERBICIDES BASED ON 2-DIBENZOFURANYLOXYALKANECARBOXYLIC ACID DERIVATIVES

[75] Inventor: John C. Saukaitis, Warwick, R.I.

[73] Assignee: American Hoechst Corporation, Somerville, N.J.

[21] Appl. No.: 943,603

[22] Filed: Sep. 18, 1978

[51] Int. Cl.$^2$ ............................................. A01N 9/22
[52] U.S. Cl. ........................................ 71/88; 260/346.71
[58] Field of Search ........................... 71/88; 260/346.71

[56] References Cited

U.S. PATENT DOCUMENTS

| | | | |
|---|---|---|---|
| 3,846,445 | 11/1974 | Bondesson et al. | 260/346.71 |
| 4,001,003 | 1/1977 | Gates | 71/88 |
| 4,097,497 | 6/1978 | Berger et al. | 260/346.71 |

Primary Examiner—Catherine L. Mills
Attorney, Agent, or Firm—Michael J. Tully

[57] ABSTRACT

The present invention relates to herbicides and herbicidal compounds based on 2-Dibenzofuranyloxyalkanecarboxylic acids and their functional derivatives having the formula:

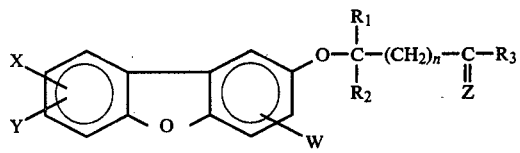

wherein:
X, Y and W are selected from the group consisting of hydrogen, halogen, ($C_1$-$C_6$) alkyl, ($C_1$-$C_6$) alkoxy, nitro, ($C_1$-$C_4$) haloalkyl, ($C_1$-$C_4$)-alkoxy-($C_1$-$C_4$)-alkyl;
$R_1$ and $R_2$ are selected from the group consisting of hydrogen and ($C_1$-$C_4$) alkyl;
Z is selected from the group consisting of oxygen and sulphur;
$R_3$ is selected from the group consisting of hydroxy; ($C_1$-$C_9$)-alkoxy wherein the alkoxy group may be substituted by from 1 to 3 of the following groups: halogen, trifluoromethyl, hydroxy, or ($C_1$-$C_4$)-alkoxy; ($C_2$-$C_8$)-alkoxyalkoxy; ($C_1$-$C_4$)-alkylthio; ($C_2$-$C_4$) alkenyloxy; cyclohexyloxy which may be substituted by a methyl group; phenoxy which may be substituted by 1-3 of the following groups: halogen, methyl, nitro, 2,4-dichlorophenoxy or methoxy; benzyloxy; amino; ($C_1$-$C_4$)-alkylamino which may be substituted by a carboxy group; di-($C_1$-$C_4$)-alkylamino; hydrazino; N',N'-di-($C_1$-$C_4$)-alkylhydrazino; anilino or pyridylamino, the phenyl or pyridylamino group of which may be substituted by 1-3 of the following groups: halogen, nitro, ($C_1$-$C_2$) alkoxy, ($C_1$-$C_2$) alkyl, hydroxy, 2,4-dichlorophenoxy or trifluoromethyl; ($C_1$-$C_4$) alkylamino; ($C_1$-$C_4$)-dialkylamino; aminotriazole; ethylene-urea; and an OM group where M is an inorganic cation or an organic base cation; and
n is 0–3.

The herbicidal compounds are preferably combined with a liquid or solid carrier material and applied either to soil or to growing plants.

7 Claims, No Drawings

HERBICIDES BASED ON 2-DIBENZOFURANYLOXYALKANECARBOXYLIC ACID DERIVATIVES

The present invention relates to herbicides and herbicidal compounds based on 2-Dibenzofuranyloxyalkanecarboxylic acids and their functional derivatives having the formula:

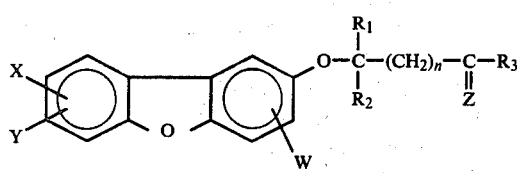

wherein:

X, Y and W are selected from the group consisting of hydrogen, halogen, ($C_1$-$C_6$) alkyl, ($C_1$-$C_6$) alkoxy, nitro, ($C_1$-$C_4$) haloalkyl, ($C_1$-$C_4$)-alkoxy-($C_1$-$C_4$)-alkyl;

$R_1$ and $R_2$ are selected from the group consisting of hydrogen and ($C_1$-$C_4$) alkyl;

Z is selected from the group consisting of oxygen and sulphur;

$R_3$ is selected from the group consisting of hydroxy; ($C_1$-$C_9$)-alkoxy wherein the alkoxy group may be substituted by from 1 to 3 of the following groups: halogen, trifluoromethyl, hydroxy, or ($C_1$-$C_4$)-alkoxy; $C_2$-$C_8$)-alkoxyalkoxy; ($C_1$-$C_4$)-alkylthio; ($C_2$-$C_4$) alkenyloxy; cyclohexyloxy which may be substituted by a methyl group; phenoxy which may be substituted by 1–3 of the following groups: halogen, methyl, nitro,2,4-dichlorophenoxy or methoxy; benzyloxy; amino ($C_1$-$C_4$)-alkylamino which may be substituted by a carboxy group; di-($C_1$-$C_4$)-alkylamino; hydrazino; N',N'-di-($C_1$-$C_4$)-alkylhydrazino; anilino or pyridylamino, the phenyl or pyridylamino group of which may be substituted by 1–3 of the following groups: halogen, nitro, ($C_1$-$C_2$) alkoxy, ($C_1$-$C_2$) alkyl, hydroxy, 2,4-dichlorophenoxy or trifluoromethyl; ($C_1$-$C_4$) alkylamino; ($C_1$-$C_4$)-dialkylamino; aminotriazole; ethylene-urea; and an OM group where M is an inorganic cation or an organic base cation; and n is 0–3.

The compounds according to Formula I, are very effective against weeds such as *Sinapis arvensis*, *Galium aparine*, *Chenopodium album*, *Matricaria chamomilla*, *Chrysanthemum segetum*, *Stellaria media*, *Amaranthus retroflexus*, while at the same time exhibiting a much improved tolerance to a number of different cultivated plants.

The compounds according to Formula I may be prepared by reacting a hydroxydibenzofuran having the general formula

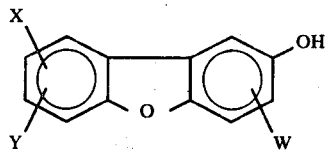

in which X, Y, and W have the meaning given above, with substituted carboxylic acid derivatives having the formula

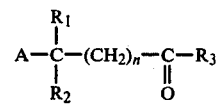

in which A is a halogen atom or an aliphatic or aromatic sulfonic acid ester group selected from the group consisting of methanesulfonate, benzenesulfonate, and p-toluenesulfonate; and in which $R_1$, $R_2$, n, and $R_3$ have the meaning given above, or by reacting compounds having the same formula II with butyrolactone having the formula

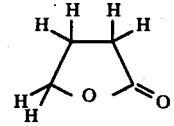

said reactions conducted in the presence of an organic or inorganic base such as potassium carbonate or an organic amine such as triethylamine.

The compounds of general Formula I are particularly suited for control of broad-leaved weeds in various agricultural and horticultural applications such as wheat, barley, oats, corn, sun flowers, peas, bush beans, and the like. In pre as well as post germination processes, they exhibit excellent herbicidal effectiveness and are superior to a series of comparable commercially available herbicidal agents.

Intermediary compounds falling within the scope of Formulas II and III are known in the art. For example, 2-hydroxydibenzofuran is disclosed by K. Schummelschmidt, Liebigs Am. Chem. 566, 184 (1950). Also, compounds such as 2-chloropropionic acid and certain of its derivatives are known as intermediaries in the preparation of herbicide compounds, particularly when reacted with certain haloaromatic compounds such as in the preparation of 2-methyl-4-chlorophenoxy propionic acid, a well known herbicide. However, agriculturalists are always seeking new herbicidal materials which exhibit an effect on a wider variety of weeds and also find a more general application to a wider variety of plants and legumes. Unfortunately, many herbicides available today are quite selective in that they are quite effective with certain plant varieties, i.e., they cause little or no damage to such plants, while at the same time causing more extensive damage to other plant varieties.

Accordingly, it is an object of the invention to provide herbicidal compounds effective for killing a wide variety of weeds and suitable for both pre and post germination applications.

Another object is to provide herbicidal compounds which are effective with a wide variety of plants and legumes while causing little or no damage to such plants and legumes.

These and other objects of the invention may be achieved by providing compounds within the scope of Formula I and combining such compounds with appropriate ingredients to form compositions suitable for the application to plants or to soil.

As indicated above, Formula I compounds may be prepared by reacting a compound having the structure of Formula II with a compound having the structure of either Formula III or Formula IV in the presence of an organic or inorganic base and preferably in a solvent medium. In the preferred embodiment, compounds particularly suitable in the present invention are those where collectively or independently:

Z is O
X is Chloro, bromo or trifluoromethane;
Y is chloro, bromo or hydrogen;
W is hydrogen;
$R_1$ and $R_2$ are hydrogen or methyl;
$R_3$ is hydroxy, $(C_1-C_6)$-alkoxy, $(C_1-C_2)$-alkoxy-$(C_1-C_3)$-alkoxy, $(C_1-C_3)$-alkythio, cyclohexyloxy, phenoxy, amino, mono or di-$(C_1-C_4)$-alkylamino or an -OM group where M represents $Na^+$, $K^+$, $NH_4^+$, $\frac{1}{2} Ca^+$ or the plant compatible cation of an organic base such as dimethylamine, triethylamine or pyridine;
A is chloro or bromo; and
n is 0 or 2.

It is preferred to conduct the above reaction using stoichiometric, usually equi molar, quantities of the reactants and in the presence of a solvent and base. Suitable solvents include acetone, methylethyl ketone, diethylketone, dimethylformamide, dimethylsulfoxide, tetrahydrofuran, benzene or toluene. The reaction is carried out in the presence of a base such as potassium carbonate, sodium methoxide, sodium hydroxide or triethylamine to generate the appropriate salt of the 2-hydroxydibenzofuran which reacts with the alkylating reactant. The reaction is preferably conducted at temperatures within the range of about 40° to 200° C., preferably 60° to 140° C.

When the reaction is complete, the salt is filtered off and the solvent is removed. The ester may be isolated and crystallized from the corresponding alcohol. The carboxylic ester thus obtained, may be converted into the carboxylic acid by hydrolysis effected using alkaline agents in aqueous alcoholic solutions at elevated temperatures. The alkaline solution may then be acidified and the crystalline product isolated by filtration. In the instance where products isolated by the procedure cited above are in the form of the carboxylic acid, the acid group can be esterified by methods known in the art such as by refluxing the acid in the presence of the desired alcohol such as in aliphatic straight or branched alcohol having from 1–6 carbon atoms or cyclohexane and also in the presence of a catalytic quantity of an acid such as sulfuric, hydrochloric, p-toluenesulfuric and the like. The carboxylic acid may also be converted to the acid chloride by reaction with thionylchloride in a solvent such as xylene or toluene. The acid chloride may then be reacted with alcohols, amines, aminotriazoles, ethyleneurea, and the like in the presence of an organic base such as triethylamine or pyridine in a solvent such as toluene, xylene or dimethylformamide.

Thio derivatives of the compound of Formula I, i.e. where Z is S, may be readily prepared by reacting the appropriate carboxylic acid derivatives with a thionating agent such as phosphorous pentasulfide or hydrogen sulfide.

The compounds prepared according to the present invention may be purified or recrystallized from organic solvents or mixtures of organic solvents with water.

As pointed out above, the herbicidal compounds of the present invention are preferably used by combining such compounds with other ingredients to form compositions which readily facilitate the application of the herbicide to plant or soil. For example, they can be applied as wettable powders, emulsified concentrates, sprayable solvents, dusting agents or as granulates. Preferably such compositions contain the herbicidal substances of Formula I at a level within the range of about 2–95% by weight.

Wettable powders may be prepared by combining the compounds of Formula I with an emulsifying agent and/or a dispersant such that the compounds may be uniformly dispersed in water. Suitable emulsifiers and dispersants include the fatty acid soaps, organic sulfonates, and like materials. Emulsions may be obtained by dissolving the compounds in an organic solvent such as butanal, cyclohexanol or an aromatic hydrocarbon and utilizing the appropriate amount of emulsifying agent where necessary. Compounds useful for dusting agents may be obtained by grinding the compounds with inert solids such as talcum, clays, or diatomaceous earth. Sprayable solutions may be prepared by simply dissolving the compounds in a suitable solvent. Granulates may be prepared by infusing the compounds into a granulated inert material or by coating solutions or concentrates containing the compounds on the surface of an absorbing substance such as sand or clay. The compounds may also be combined with a fertilizer where it is desired to apply the material to soil prior to crop germination.

The concentration of the herbicidal compound of Formula I in such compositions may vary widely, depending on the manner in which it is to be used commercially. In wettable powders the concentration can vary between 10 and 80% by weight. In emulsions, the best concentration is about 10 to 70% by weight. In dusting powders, the preferred concentration is about 5–20% by weight.

The amount of the compounds of Formula I which must be applied per hectacre to effectively control weeds may vary depending on weather conditions of temperature and humidity, but generally, quantities with the range of 0.1 to 10.0 kgs/hectacre are suitable. The materials are preferably applied in the range of 0.3 to 5.0 kgs/hectacre.

The following examples are illustrative of the invention. The various methods of preparation of compounds within the scope of Formula I are illustrated in the following syntheses A through H. Table I sets forth 74 Examples illustrating the preparation of compounds within the scope of the invention and makes reference to the analogous A through H method by which the various compounds were prepared. Note that in all cases in these examples that W is hydrogen.

EXAMPLE A

Isopropyl-2-(7-chloro-2-dibenzofuranyloxy) propionate 15.2 g (0.07 mole) 7-chloro-2-hydroxydibenzofuran are dissolved in 125 ml of xylene. To this solution is added 15.12 g of sodium methoxide solution. The mixture is heated to 125° C. and the methanol is distilled off. 13.65 g (0.07 mole) of isopropyl-2-bromopropionate is added dropwise over a 5 minute period. The temperature is held at 125° C. for 1.5 hours. The solution is filtered free of salts and the solvent evaporated. The crude product is crystallized from methylene chloride/hexane. 13.4 g of isopropyl-2-(7-chloro-2-dibenzofuranyloxypropionate), m.p. 87°–89° C. is obtained. The Example corresponds to Example 12 in Table I.

EXAMPLE B

2-(7-Chloro-2-dibenzofuranyloxy) propionamide 21.7 g (0.1 mole) 7-chloro-2-hydroxydibenzofuran is dissolved in 200 ml of tetrahydrofuran. To this solution is added 5.2 g sodium hydride (50% dispersion in oil) which was prewashed in petroleum ether. After hydrogen evolution had ceased, the solution was brought to reflux and 11.2 g (0.1 mole) of 2-chloropropionamide was added. The mixture was allowed to reflux for 8 hours. The solvent was evaporated and the crude product was washed with dilute acid and crystallized from methanol to yield 14.5 g, m.p. 185°–187° C. This Example corresponds to Example 20 in Table I.

EXAMPLE C

2-(7-Chloro-2-dibenzofuranyloxy) propionic acid 29 g (0.1 mole) Methyl-2-(7-chloro-2-dibenzofuranyloxy) propionate is dissolved in 200 ml of methanol. To this solution is added a solution containing 8 g (0.2 mole) sodium hydroxide pellets dissolved in 100 ml of water. This mixture is heated to 50° C. for one hour and then poured into dilute acid. The solid is collected and washed with methanol. 20 g., m.p. 170°–172° C. are obtained after drying. This Example corresponds to Example 33 in Table I.

EXAMPLE D

2-(7-Chloro-2-dibenzofuranyloxy) butyric acid 110 g (0.5 mole) 7-Chloro-2-hydroxydibenzofuran is dissolved in 200 g (2.3 mole) of butyrolactone. To this solution is added 27.5 g (0.57 mole) sodium hydride 50% dispersion in oil (prewashed with petroleum ether) in small increments. When hydrogen evolution ceases the solution is heated to 120° C. for 2 hours. The excess butyrolactone was distilled off under high vacuum. The crude product was dissolved in water and precipitated into dilute acid. The product was filtered and redissolved in sodium bicarbonate solution. The solution was charcoal treated and precipitated in dilute acid filtered and dried. 137 g., m.p. 143°–145° C. were obtained. This Example corresponds to Example 69 in Table I.

EXAMPLE E

(N-3-Trifluoromethylphenyl)-2-(7-chloro-2-dibenzofuranyloxy) Propionamide 10 g (0.035 mole) of 2-(7-chloro-2-dibenzofuranyloxy)-propionic acid is slurried in 125 ml of toluene. To this mixture is added 4.6 g (0.038 mole) thionyl chloride. The mixture is brought to reflux and all the contents dissolve. 25 ml of toluene are collected with a dean stark trap. To this solution is added a solution containing 5.6 g (0.035 mole) 3-trifluoromethylaniline and 3.1 g (0.038 mole) pyridine dissolved in 50 ml of toluene at room temperature. After addition was complete the reaction was allowed to stir for an additional 2 hours. The solvent was distilled and the crude product slurried in methanol and filtered to yield 11.8 g., m.p. 171°–174° C. This Example corresponds to Example 48 in Table I.

EXAMPLE F

Isopropyl-4-(7-bromo-2-dibenzofuranyloxy) butyrate 10 g (0.029 mole) 4-(7-bromo-2-dibenzofuranyloxy) butyric acid is slurried in 200 ml of isopropanol. To this mixture is added 0.5 g 100% sulfuric acid. The mixture is brought to reflux, the contents dissolved, reflux is continued for 30 minutes. The solution is then allowed to cool and the isopropyl-4-(7-bromo-2-dibenzofuranyloxy) butyrate crystallizes. 10.5 g. are obtained, m.p. 67°–74° C. This Example corresponds to Example 73 in Table I.

EXAMPLE G

N[2-(7-Chloro-2-dibenzofuranyloxy) propionyl]-4-amino-1,2,4-triazole 10.85 g. (0.035 mole) of α-7-Chloro-2-dibenzofuranyloxypropionyl chloride is dissolved in 100 ml. of toluene. To this solution is added a solution containing 2.94 g. (0.035 mole) 4-amino-1,2,4-triazole and 3.5 g. (0.035 mole) triethylamine dissolved in 50 ml. of dimethylformamide. After addition is complete the reaction is allowed to stir for an additional 2 hours. The solvent is removed and the crude product slurried in methanol. 8.1 g. are obtained, m.p. 215°–218° C. This Example corresponds to Example 57 in Table I.

EXAMPLE H.

N-Butyl-2-(7-chloro-2-dibenzofuranyloxy) thiopropionamide 20 g. (0.058 mole) N-Butyl-2-(7-chloro-2-dibenzofuranyloxy) propionamide was dissolved in 100 ml. of pyridine. To this solution is added 14.2 g. (0.064 mole) phosphorous pentasulfide. The mixture is refluxed for 2.5 hours, the solvent removed and the remaining mixture drowned in dilute hydrochloric acid. The crude product is filtered and crystallized from methanol to yield 6.1 g. m.p. 101°–104° C. This Example corresponds to Example 60 in Table I.

TABLE I

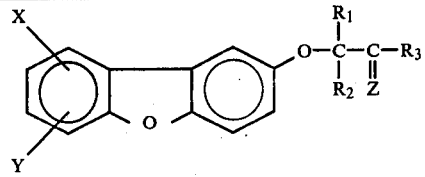

| Example Number | X | Y | Z | $R_1$ | $R_2$ | $R_3$ | Analogous Production Example | m.p.(°C.) |
|---|---|---|---|---|---|---|---|---|
| 1 | 9-Cl | H | O | —CH$_3$ | H | —OCH$_3$ | A | 73°–74° |
| 2 | 9-Cl | H | O | —CH$_3$ | H | —OC$_2$H$_5$ | A | 53.5°–54° |
| 3 | 8-Cl | H | O | —CH$_3$ | H | —OCH$_3$ | A | 71°–72° |
| 4 | 8-Cl | H | O | —CH$_3$ | H | —OC$_2$H$_5$ | A | 87°–90° |
| 5 | 8-CF$_3$ | H | O | —CH$_3$ | H | —OCH$_3$ | A | 77°–80° |
| 6 | 7-Cl | H | O | H | H | —OCH$_3$ | A | 114°–117° |
| 7 | 7-Cl | H | O | H | H | —OC$_2$H$_5$ | A | 121°–126° |

TABLE I-continued

Structure: dibenzofuran core with X at upper-left ring, Y at lower-left ring, and on the right ring: $-O-C(R_1)(R_2)-C(=Z)-R_3$

| Example Number | X | Y | Z | $R_1$ | $R_2$ | $R_3$ | Analogous Production Example | m.p.(°C.) |
|---|---|---|---|---|---|---|---|---|
| 8 | 7-Cl | H | O | H | H | $-OCH(CH_3)_2$ | A | 112°–116° |
| 9 | 7-Cl | H | O | $-CH_3$ | H | $-OCH_3$ | A | 105°–106° |
| 10 | 7-Cl | H | O | $-CH_3$ | H | $-OC_2H_5$ | A | 75°–76° |
| 11 | 7-Cl | H | O | $-CH_3$ | H | $-OC_3H_7(n)$ | A | 57°–58° |
| 12 | 7-Cl | H | O | $-CH_3$ | H | $-OCH(CH_3)_2$ | A | 87°–89° |
| 13 | 7-Cl | H | O | $-CH_3$ | H | $-OC_4H_9(n)$ | A | 86,5°–87,5° |
| 14 | 7-Cl | H | O | $-CH_3$ | H | $-O-CH_2-CH(CH_3)_2$ | A | 57°–60° |
| 15 | 7-Cl | H | O | $-CH_3$ | H | $-O-CH(CH_3)-C_2H_5$ | A | 96°–100° |
| 16 | 7-Cl | H | O | $-CH_3$ | H | $-OC_5H_{11}(n)$ | A | 48°–51° |
| 17 | 7-Cl | H | O | $-CH_3$ | H | $-O(CH_2)_3-CH(CH_3)_2$ | A | 68°–69° |
| 18 | 7-Cl | H | O | $-CH_3$ | H | $-O(CH_2)_2-OCH_3$ | A | 40°–44° |
| 19 | 7-Cl | H | O | $-CH_3$ | H | $-O(CH_2)_2-OC_2H_5$ | A | 49°–54° |
| 20 | 7-Cl | H | O | $-CH_3$ | H | $-NH_2$ | B | 185°–187° |
| 21 | 6-Cl | H | O | $-CH_3$ | H | $-OCH_3$ | A | 94°–95° |
| 22 | 6-Cl | H | O | $-CH_3$ | H | $-OC_2H_5$ | A | 91°–94° |
| 23 | 9-Cl | 7-Cl | O | $-CH_3$ | H | $-OCH_3$ | A | 91,5°–92,5° |
| 24 | 9-Cl | 7-Cl | O | $-CH_3$ | H | $-OC_2H_5$ | A | 78°–80° |
| 25 | 8-Cl | 7-Cl | O | $-CH_3$ | H | $-OC_2H_5$ | A | 106°–107° |
| 26 | 8-Cl | 7-Cl | O | $-CH_3$ | H | $-OCH_3$ | A | 109,5°–111,5° |
| 27 | 7-Br | H | O | H | H | $-OCH_3$ | A | 127°–130° |
| 28 | 7-Br | H | O | H | H | $-OC_2H_5$ | A | 124°–129° |
| 29 | 7-Br | H | O | $-CH_3$ | H | $-OCH_3$ | A | 98°–100° |
| 30 | 7-Br | H | O | $-CH_3$ | H | $-OC_2H_5$ | A | 66°–69° |
| 31 | 9-Br | 7-Br | O | $-CH_3$ | H | $-OC_2H_5$ | A | 83°–84° |
| 32 | 9-Br | 7-Br | O | $-CH_3$ | H | $-OCH_3$ | A | 104,5°–106,5° |
| 33 | 7-Cl | H | O | $-CH_3$ | H | $-OH$ | C | 170°–172° |
| 34 | 7-Cl | H | O | $-CH_3$ | $-CH_3$ | $O-CH_2-CF_3$ | F | 100°–103° C. |
| 35 | 7-$CH_3$ | H | O | $-CH_3$ | H | $-OCH_3$ | A | 69°–73° |
| 36 | 7-Cl | H | O | $-CH_3$ | H | $-NH-CH_3$ | E | 147°–157° |
| 37 | 7-Cl | H | O | $-CH_3$ | H | $-NH-C_2H_5$ | E | 137°–140° |
| 38 | 7-Cl | H | O | $-CH_3$ | H | $-N(CH_3)_2$ | E | 99°–101° |
| 39 | 7-Cl | H | O | $-CH_3$ | H | $-N(C_2H_5)_2$ | E | 105°–109° |
| 40 | 7-Cl | H | O | $-CH_3$ | H | $-NH-C_6H_4-Cl$ (4-Cl) | E | 157°–159° |
| 41 | 7-Cl | H | O | $-CH_3$ | H | $-NH-C_6H_3-Cl_2$ (2,4-Cl) | E | 131°–134° |
| 42 | 7-Cl | H | O | $-CH_3$ | H | $NH(CH_2)_2-CH_3$ | E | 153°–155° |
| 43 | 7-Cl | H | O | $-CH_3$ | H | $NH(CH_2)_3-CH_3$ | E | 165.5°–167° |
| 44 | 7-Cl | H | O | $-CH_3$ | H | $-NH-C_6H_3-Cl_2$ (3,4-Cl) | E | 152°–155° |
| 45 | 7-Cl | H | O | $-CH_3$ | H | $-NH-C_6H_4-Br$ (4-Br) | E | 160°–162° |
| 46 | 7-Cl | H | O | $-CH_3$ | H | $-NH-C_6H_4-F$ (4-F) | E | 157°–159° |
| 47 | 7-Cl | H | O | $-CH_3$ | H | $-NH-C_6H_3(Cl)(Br)$ (2-Cl, 4-Br) | E | 144°–146° |

TABLE I-continued

Structure:

X, Y substituted dibenzofuran with -O-C(R1)(R2)-C(=Z)-R3 side chain

| Example Number | X | Y | Z | R₁ | R₂ | R₃ | Analogous Production Example | m.p.(°C.) |
|---|---|---|---|---|---|---|---|---|
| 48 | 7-Cl | H | O | —CH₃ | H | —NH—C₆H₄—CF₃ (3-CF₃) | E | 171°–174° |
| 49 | 7-Cl | H | O | —CH₃ | H | —NH—C₆H₄—CF₃ (4-CF₃) | E | 167°–171° |
| 50 | 7-Cl | H | O | —CH₃ | H | —NH—C₆H₃(CF₃)₂ (3,5-(CF₃)₂) | E | 174°–176° |
| 51 | 7-Cl | H | O | —CH₃ | H | —NH—C₆H₃(Cl)(CF₃) (2-Cl, 5-CF₃) | E | 153°–156° |
| 52 | 7-Cl | H | O | —CH₃ | H | —NH—C₆H₃(Cl)(OCH₃) (2-Cl, 4-OCH₃) | E | 173°–175° |
| 53 | 7-Cl | H | O | —CH₃ | H | —NH—C₆H₃(Cl)(NO₂) (2-Cl, 4-NO₂) | E | 168°–170° |
| 54 | 7-Cl | H | O | —CH₃ | H | —NH—(3,5-dichloropyridin-2-yl) | E | 194°–196° |
| 55 | 7-Cl | H | O | —CH₃ | H | —NH—C₆H₃(CH₃)₂ (2,6-(CH₃)₂) | E | 223°–224° |
| 56 | 7-Cl | H | O | —CH₃ | H | —NH—C₆H₃(C₂H₅)₂ (2,6-(C₂H₅)₂) | E | 157°–159° |

TABLE I-continued

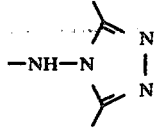

| Example Number | X | Y | Z | R₁ | R₂ | R₃ | Analogous Production Example | m.p.(°C.) |
|---|---|---|---|---|---|---|---|---|
| 57 | 7-Cl | H | O | —CH₃ | H | (triazole-NH-N structure) | G | 215°–218° C. |
| 58 | 7-Cl | H | O | —CH₃ | H | (triazole NH structure) | G | 257°–259° C. |
| 59 | 7-Cl | H | O | —CH₃ | H | (CH₂—CH₂—N—NH—C=O ring) | G | 208°–211° C. |
| 60 | 7-Cl | H | S | —CH₃ | H | —NH(CH₂)₃—CH₃ | H | 101°–104° C. |
| 61 | 7-Cl | H | S | —CH₃ | H | —NHCH₂—CH₃ | H | 92°–96° C. |
| 62 | 7-Cl | H | O | —CH₃ | H | —NH—(C₆H₄)—O—(C₆H₃Cl₂) | E | 168°–169.5° |
| 63 | 7-Cl | H | O | —CH₃ | H | —O—(C₆H₄)—O—(C₆H₃Cl₂) | E | 120.5°–124° C. |

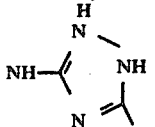

| Example Number | X | Y | Z | R₁ | R₂ | R₃ | Analogous Production Example | m.p.(°C.) |
|---|---|---|---|---|---|---|---|---|
| 64 | 7-Cl | H | O | H | H | —OCH₃ | F | 69.5°–70.5° |
| 65 | 7-Cl | H | O | H | H | —OC₂H₅ | F | 58°–60° |
| 66 | 7-Cl | H | O | H | H | —OC₃H₇(n) | F | 67°–68° |
| 67 | 7-Cl | H | O | H | H | —OC₃H₇(i) | F | 69°–71° |
| 68 | 7-Cl | H | O | H | H | —OC₄H₉(sec.) | F | 52°–54° |
| 69 | 7-Cl | H | O | H | H | —OH | D | 143°–145° |
| 70 | 7-Br | H | O | H | H | —OCH₃ | F | 65°–68° |
| 71 | 7-Br | H | O | H | H | —OC₂H₅ | F | 65°–68° |
| 72 | 7-Br | H | O | H | H | —OC₃H₇(n) | | |
| 73 | 7-Br | H | O | H | H | —OC₃H₇(i) | F | 67°–74° |
| 74 | 7-Br | H | O | H | H· | —OH | D | 134°–137° |

As indicated above, the compounds of the invention may be readily formulated to provide compositions suitable for application to plants or soil. For example, water dispersible powders may be prepared by co-grinding a composition containing about 25 parts by weight of the herbicidal compound, 64 parts by weight of quartz, 10 parts by weight of the potassium salt of lignum-sulfonic acid, and 1 part by weight of sodium N-methyl-N-oleoyl taurate as wetting or dispersing agents. Dusting agents may be prepared by co-grinding a mixture of about 10 parts by weight of the herbicidal compound and 90 parts by weight of a talc carrier mixture. An emulsifiable concentrate may be prepared by forming a dispersion containing about 15 parts by weight of the herbicidal compound, 75 parts by weight cyclohexanone, and 10 parts by weight of oxyethylated nonylphenol as an emulsifier. An effective granulate material may contain about 7 parts by weight of the herbicidal compound and 93 parts by weight of pumice or quartz.

In order to demonstrate the herbicidal effectiveness of the compounds within the scope of this invention, a representative series of samples were prepared and tested in both pre and post germination applications.

For the pre-germination test, seeds of various weeds and cultivated plants were sowed out into containers and covered with soil. The soil surface was then treated with an aqueous dispersion containing the compounds of this invention as indicated in Table III, applied at levels such that the effective dosage of the compounds is approximately 2.5 kg/hectacre and 0.62 kg/hectacre respectively. A control herbicide, 2-methyl-4-chlorophenoxy-propionic acid was applied the same way and at the same levels. Four weeks after the treatment, the condition of the plants and weeds was evaluated according to the pattern from Bolle, (Report Sheet of the German Plant Protection Service 16, 1964, 92–94). Under this system, a series of value figures is assigned corresponding to the visual condition of the plants and weeds as illustrated in Table II.

Table II

| Value Figure | Damage Effectiveness in % on | |
|---|---|---|
| | Weeds | Cultivated Plants |
| 1 | 100 | 0 |
| 2 | 97.5 to <100 | >0 to 2.5 |
| 3 | 95 to <97.5 | >2.5 to 5 |
| 4 | 90 59 <95 | >5 to 10 |
| 5 | 85 to <90 | >10 to 15 |
| 6 | 75 to <85 | >15 to 25 |
| 7 | 65 to <75 | >25 to 35 |
| 8 | 32.5 to <65 | >35 to 67.5 |
| 9 | 0 to <32.5 | >67.5 to 100 |

The values given in Table III show that compounds according to the invention are very effective against weeds at a dosage level of 2.5 kg/hectacre and also exhibit effectiveness at 0.62 kg/hectacre, while at the same time causing litte or no damage to the valuable crops. Test results of the control compound were not nearly as good.

Table III

| Compound according to Example: | No. 9 | | No. 10 | | No. 23 | | Control | |
|---|---|---|---|---|---|---|---|---|
| | 2.5 | 0.62 | 2.5 | 0.62 | 2.5 | 0.62 | 2.5 | 0.62 |
| *Sinapis arvensis* | 2 | 4 | 2 | 3 | — | — | 1 | 3 |
| *Galium aparine* | 1 | 1 | 1 | 2 | — | — | 1 | 3 |
| *Chenopodium album* | 1 | 3 | 1 | 1 | 1 | 1 | 4 | 6 |
| *Matricaria chamomilla* | 1 | 2 | 1 | 2 | 1 | 4 | 2 | 4 |
| *Chrysanthemum segetum* | 3 | 7 | 3 | 6 | — | — | 4 | 6 |
| *Stellaria media* | 3 | 8 | 2 | 4 | — | — | 1 | 3 |
| *Amaranthus retroflexus* | 1 | 1 | 1 | 1 | 1 | 4 | 3 | 4 |
| Wheat | 1 | 1 | 3 | 1 | — | — | 5 | 4 |
| Barley | 1 | 1 | 2 | 1 | — | — | 6 | 3 |
| Oats | 1 | 1 | 1 | 1 | — | — | 6 | 3 |
| Corn | 1 | 1 | 2 | 1 | — | — | 6 | 4 |
| Sunflower | 1 | 1 | 3 | 1 | — | — | 6 | 4 |
| Peas | 3 | 1 | 2 | 1 | — | — | 9 | 8 |
| Bush Beans | 2 | 1 | 3 | 2 | — | — | 5 | 3 |

In a test similar to that above, aqueous dispersions containing certain of the herbicidal compounds of this invention were employed in a post-germination application by spraying on previously untreated plants and Chenopodium weeds at various dose levels. The effect on the weeds after a short period of time is shown in Table IV.

Table IV

| Compound of Ex.: | 9 | 10 | 23 | 24 | 26 | 31 | 32 |
|---|---|---|---|---|---|---|---|
| Dose level 0.6 | 3 | 1 | 4 | 4 | — | — | 3 |
| Kg./ha. 1.25 | — | — | — | — | 5 | 5 | — |
| 2.50 | 2 | 1 | 3 | 4 | — | — | 2 |

What I claim is:

1. A method for controlling the development of weeds in plants and legumes comprising applying to said plants and legumes or to soil in which said plants and legumes are grown, an effective amount of a herbicidal composition containing, as a herbicidally active ingredient, a compound having the formula:

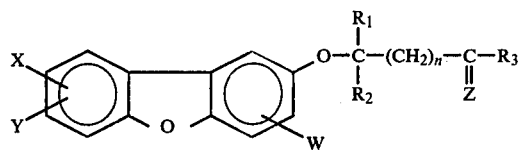

wherein:
X, Y and W are selected from the group consisting of hydrogen, halogen, ($C_1$-$C_6$) alkyl, ($C_1$-$C_6$) alkoxy, nitro, ($C_1$-$C_4$) haloalkyl, ($C_1$-$C_4$)-alkoxy-($C_1$-$C_4$)-alkyl;

$R_1$ and $R_2$ are selected from the group consisting of hydrogen and ($C_1$-$C_4$) alkyl;

Z is selected from the group consisting of oxygen and sulphur;

$R_3$ is selected from the group consisting of hydroxy; ($C_1$-$C_9$)-alkoxy wherein the alkoxy group may be substituted by from 1 to 3 of the following groups: halogen, trifluoromethyl, hydroxy, or ($C_1$-$C_4$)-alkoxy; ($C_2$-$C_8$)-alkoxyalkoxy; ($C_1$-$C_4$)-alkylthio; ($C_2$-$C_4$) alkenyloxy; cyclohexyloxy which may be substituted by a methyl group; phenoxy which may be substituted by 1–3 of the following groups: halogen, methyl, nitro,2,4-dichlorophenoxy or methoxy; benzyloxy; amino; ($C_1$-$C_4$)-alkylamino which may be substituted by a carboxy group; di-($C_1$-$C_4$)-alkylamino; hydrazino; N',N'-di-($C_1$-$C_4$)-alkylhydrazino; anilino or pyridylamino, the phenyl or pyridylamino group of which may be substituted by 1–3 of the following groups: halogen, nitro, ($C_1$-$C_2$) alkoxy, ($C_1$-$C_2$) alkyl, hydroxy, 2,4-dichlorophenoxy or trifluoromethyl; ($C_1$-$C_4$) alkylamino; ($C_1$-$C_4$)-dialkylamino; aminotriazole; ethylene-urea; and an OM group where M is an inorganic cation or an organic base cation; and n is 0–3.

2. The method of claim 1 wherein:
X is selected from the group consisting of 7-Cl or 7-Br;
W and Y are each hydrogen;
Z is oxygen
$R_1$ is methyl;
$R_2$ is hydrogen;
$R_3$ is ($C_1$-$C_9$) alkoxy; and
n is 0 or 2.

3. The method of claim 2 wherein:
X is 7-Cl;
$R_3$ is —OCH$_3$; and
n is 0.

4. The method of claim 2 wherein:
X is 7-Cl;
$R_3$ is —OC$_2$H$_5$; and n is 0.
5. The method of claim 2 wherein:
X is 7-Cl;
$R_3$ is $-OC_3H_7$; and
n is 0.
6. The method of claim 2 wherein:
X is 7-Br;
$R_3$ is $-OCH_3$; and
n is 0.
7. The method of claim 2 wherein:
X is 7-Br;
$R_3$ is $-OC_2H_5$; and
n is 0.

* * * * *